United States Patent [19]

Miyata

[11] Patent Number: 4,514,389

[45] Date of Patent: Apr. 30, 1985

[54] GASTRIC ANTACID AND METHOD FOR CONTROLLING PH OF GASTRIC JUICE

[75] Inventor: Shigeo Miyata, Takamatsu, Japan

[73] Assignee: Kyowa Chemical Industry Co. Ltd., Tokyo, Japan

[21] Appl. No.: 439,993

[22] Filed: Nov. 8, 1982

Related U.S. Application Data

[63] Continuation-in-part of Ser. No. 260,887, May 6, 1981, abandoned.

[51] Int. Cl.$^3$ .......................................... A61K 33/42
[52] U.S. Cl. ................................ 424/128; 423/419 P; 423/544; 423/306; 423/600; 424/156; 424/157
[58] Field of Search ................ 423/600, 419 P, 544, 423/306; 424/128, 156, 157

[56] References Cited

U.S. PATENT DOCUMENTS

| | | | |
|---|---|---|---|
| 2,958,626 | 11/1960 | Schenck et al. | 424/156 |
| 3,099,524 | 7/1963 | Grossmith | 424/156 |
| 3,239,416 | 3/1966 | Rubino | 424/156 X |
| 3,539,306 | 11/1970 | Kumura et al. | 424/156 |
| 3,650,704 | 3/1972 | Kumura et al. | 424/156 X |
| 3,879,525 | 4/1975 | Miyata et al. | 424/156 X |
| 3,980,685 | 9/1974 | Miyata et al. | 424/230 |

FOREIGN PATENT DOCUMENTS 1185920  3/1970  United Kingdom ................ 424/156

*Primary Examiner*—Frederick E. Waddell
*Attorney, Agent, or Firm*—Sherman & Shalloway

[57] ABSTRACT

A pharmaceutical composition comprising an amount, effective as an antacid, of a phosphate ion-containing hydrotalcite of the following formula $$Mg_xAl_2(OH)_{2x+6-n_1z_1-n_2z_2}(A_1{}^{n_1-})_{z_1}(A_2{}^{n_2-})_{z_2} \cdot mH_2O$$

wherein $A_1{}^{n_1-}$ represents at least one anion having a valence of $n_1$ selected from the group consisting of $H_2PO_4{}^-$, $HPO_4{}^{2-}$ and $PO_4{}^{-3}$, $A_2{}^{n_2-}$ represents at least one anion having a valence of $n_2$ other than the $A_1{}^{n_1-}$, and x, $z_1$, $z_2$, and m are positive numbers satisfying the following expressions $$2 < x < 40,$$

$$0.05 \leq z_1 \leq 2,$$

$$0.1 \leq z_2 < 2,$$

$$0 < m < 40,$$

$$0.5 \leq z_1 + z_2 \leq 2,$$

and a pharmaceutically acceptable diluent or carrier; and a method for controlling the pH of gastric juice, using the aforesaid phosphate ion-containing hydrotalcite.

9 Claims, No Drawings

GASTRIC ANTACID AND METHOD FOR CONTROLLING PH OF GASTRIC JUICE

This application is a continuation-in-part application of U.S. Ser. No. 260,887 filed on May 6, 1981 now abandoned.

This invention relates to a new type of gastric antacid which exhibits a rapid and long-lasting buffering action of controlling the pH of gastric juice to an ideal pH range without any likelihood of causing undesirable side-effects such as osteomalacia, or phosphoric-deficient syndrome including hypophosphoremia, hypophosphaturia, hypercalcinuria, anepithymia, etc.

More specifically, this invention relates to a pharmaceutical composition comprising an amount, effective as an antacid, of a phosphate ion-containing hydrotalcite of the following formula $$Mg_xAl_2(OH)_{2x+6-n_1z_1-n_2z_2}(A_1^{n_1-})_{z_1}(A_2^{n_2-})_{z_2}\cdot mH_2O \quad (1)$$

wherein $A_1^{n_1-}$ represents at least one anion having a valence of $n_1$ selected from the group consisting of $H_2PO_4^-$, $HPO_4^{2-}$ and $PO_4^{-3}$, $A_2^{n_2-}$ represents at least one anion having a valence of $n_2$ other than the $A_1^{n_1-}$, and x, $z_1$, $z_2$, and m are positive numbers satisfying the following expressions $2 < x < 40,$ $0.05 \leq z_1 \leq 2,$ $0.1 \leq z_2 < 2,$ $0 < m < 40,$ $0.5 \leq z_1 + z_2 \leq 2,$ and a pharmaceutically acceptable diluent or carrier.

The present invention also pertains to a method for controlling the pH of gastric juice which comprises orally administering the phosphate ion-containing hydrotalcite of formula (1), and to the phosphate ion-containing hydrotalcite of formula (1) for use in treating gastric juice.

Gastric antacids are used in the treatment of gastric juice including prevention and treatment of gastricisms such as gastritis, gastric ulcer and duodenal ulcer by neutralizing and buffering the pH of gastric juice. The present invention relates to an antacid which is useful in such applications and has excellent activity without likelihood to cause undesirable side-effects such as osteomalacia or phosphoric-deficient syndrome.

Antacids are required to rapidly neutralize and buffer the pH of gastric juice to a pH value at which pepsin is inactivated with a long-lasting effect, and should also desirably be stable compounds whose properties do not change over a long period of time and which have a low content of sodium that may cause hypertension.

Aluminum-containing compounds have been used heretofore as antacids. Most typical of these are aluminum hydroxide gel or cogels containing aluminum hydroxide gel prepared by co-precipitation (U.S. Pat. Nos. 2,958,626; 3,099,524; and 3,239,416) and hydrotalcite [$Mg_6Al_2(OH_{16}CO_3\cdot 4H_2O$] (U.S. Pat. Nos. 3,539,306 and 3,650,704; British Patent No. 1,185,920). The former is oldest, and is still used most frequently throughout the world. The latter attracted attention as a better antacid than the former, and its use has recently increased.

The increasing acceptance of the latter is due to the fact that it has better stability and has a better action of neutralizing and buffering gastric acid. Aluminum hydroxide gel or cogel is an unstable amorphous compound. Immediately after production, its antacid activity is excellent. But since it gradually crystallizes to aluminum hydroxide, its original antacid activity is lost with time. The former also has the defect that because it can control the pH of gastric acid only to a range of about 3 to 4, its activity to inhibit the action of pepsin in gastric juice is not sufficient. In contrast, because hydrotalcite is a stable crystalline compound which is stable to heat, light, water, etc., it has the advantage that even after the lapse of a long period of time from preparation, its antacid activity is not reduced. Furthermore, hydrotalcite can control the pH of gastric acid to an ideal range of about 3 to 5, and therefore, its action of inactivating pepsin in gastric juice is sufficient, thus bringing about the advantage that the undesirable activity of pepsin on the stomachal wall tissue can be fully inhibited.

It has recently been found however that long-term continued administration of an aluminum-containing antacid causes side-effects resulting in osteomalacia and phosphoric-deficient syndrome including hypophosphoremia, hypophosphaturia, hypercalcinuria, anepithymia, etc. These side-effects occur presumably because an aluminum ion derived from the aluminum-containing antacid and dissolved in gastric juice captures a phosphate ion to be absorbed as calcium phosphate as a main ingredient of the skeleton to form insoluble aluminum phosphate which inhibits absorption of the phosphate ion into the body.

U.S. Pat. No. 3,879,525 describes a composite metal hydroxide containing a divalent inorganic anion other than $CO_3^{2-}$, and shows its utility as an antacid. This U.S. Patent exemplifies $HPO_4^{2-}$ as the inorganic anion, and Example 18 shows $Mg_6Al_2(OH)_{16}HPO_4\cdot 4H_2O$. The Patent, however, is quite silent on a compound containing both a phosphate and a carbonate ion, and the composite metal hydroxide of this Patent does not show satisfactory antacid activity.

The present inventors made investigations in order to develop a new type of antacid which is free from the aforesaid disadvantages and troubles of the conventional aluminum-containing antacids. These investigations have led to the discovery that hydrotalcite-like compounds containing two kinds of anions ($A_1^{n_1-}$) and ($A_2^{n_2-}$) (to be sometimes referred to in the present application as phosphate ion-containing hydrotalcites) conveniently free from the undesirable side-effects of causing the aforesaid phosphoric-deficient syndrome and osteomalacia, and have a rapid and long-lasting activity of neutralizing and buffering the pH of gastric juice to an ideal range of about 3 to about 5; and therefore that they are very useful for prevention, and treatment of a broad ranges of gastricisms such as gastritis, gastric ulcer and duodenal ulcer while inhibiting the undesirable action of pepsin on the stomachal wall tissue.

The phosphate ion-containing hydrotalcites of formula (1) in accordance with this invention have the advantage that they are very stable to light, heat, water, etc. and for example, have stability to heat of up to about 300° C. and on long-term storage, do not decrease in antacid activity owing to aging. Furthermore, these hydrotalcites do not at all cause a side-effect of constipation which is seen in the administration of aluminum hydroxide gel nor a lapactic action which is seen in the administration of magnesium hydroxide or magnesium oxide presumably because these actions conveniently negate each other in these hydrotalcites. Moreover, since the sodium content of these phosphate ion-containing hydrotalcites is only a trace which can substantially be neglected, they are not likely to cause a side-effect attributed to sodium even when administered to persons with hypertension, cardiovascular troubles, renal troubles, etc.

It is an object of this invention therefore to provide a new-type of antacid having the above advantages.

The above and other objects of the invention are apparent from the following description.

The phosphate ion-containing hydroaltalcites in accordance with this invention are represented by the following formula $$Mg_xAl_2(OH)_{2x+6-n_1z_1-n_2z_2}(A_1^{n_1-})_{z_1}(A_2^{n_2-})_{z_2} \cdot mH_2O \quad (1)$$

wherein $A_1^{n_1-}$ represents at least one anion having a valence of $n_1$ selected from the group consisting of $H_2PO_4^-$, $HPO_4^{2-}$ and $PO_4^{3-}$, $A_2^{n_2-}$ represents at least one anion having a valence of $n_2$ other than the anion $A_1^{n_1-}$, and x, $z_1$, $z_2$ and m are positive numbers which satisfy the following expressions $2<x<40$, preferably $3 \leq x \leq 10$, more preferably $4 \leq x \leq 8$, $0.05 \leq z_1 \leq 2$, preferably $0.08 \leq z_1 \leq 1$, more preferably $0.1 \leq z_1 \leq 0.5$, $0.1 \leq z_2 < 2$, preferably $0.1 \leq z_2 \leq 1.5$, more preferably $0.5 \leq z_2 \leq 1.2$, $0<m<40$, preferably $0.5 \leq m<40$, $0.5 \leq z_1+z_2 \leq 2$, preferably $0.8 \leq z_1+z_2 \leq 1.5$.

Examples of the anion $A_2^{n_2-}$ are inorganic acid ions other than $A_1^{n_1-}$, preferably carbonate ions, $C_2$-$C_{10}$ organic carboxylic acid or amino acid ions.

Examples of preferred anions $A_2$ are $CO_3^{2-}$, tartrate ion $(CHOHCOO)_3^{2-}$, salicylate ion $C_6H_5(OH)COO^-$, citrate ion $C_3H_4OH(COO)_3^{3-}$, glycine ion $NH_2CH_2COO^-$, glutamate ion $C_5H_7NO_4^{2-}$, cystine ion $C_3H_6NO_2S^-$, lactate ion $CH_3CHOHCOO^-$, and malate ion $CHOHCH_2(COO)_2^{2-}$.

Hydrotalcite-like compounds having these two kinds of anions can be produced by the analogous process described, for example in Japanese Patent Publication No. 32198/1972 (U.S. Pat. No. 3,875,525, British Patent No. 1,336,865), Japanese Patent Publications Nos. 29477/1973 and 29478/1973, Miyata, Clays and Clay Minerals, Vol. 23, pages 369–375 (1975), and Miyata, Clays and Clay Minerals, Vol. 25, pages 14–18 (1977).

Briefly stated, the phosphate ion-containing hydrotalcite of formula (1) can be produced, for example, by reacting an aluminum compound, preferably a water-soluble aluminum or magnesium compound, with phosphoric acid or its alkali metal or ammonium salt in a liquid medium, preferably in an aqueous medium, under such conditions that the pH of the reaction system is at least about 8. If required, after the reaction, the product may be subjected to various steps such as solvent removal, washing with water, drying, pulverization, and classification.

In another embodiment, a phosphate ion-free hydrotalcite of the following formula $$Mg_xAl_2(OH)_{2x+6-n_3z_3}(A_3^{n_3-})_{z_3} \cdot mH_2O \quad (1')$$

wherein x and m are as defined with regard to formula (1), $n_3$ and $z_3$ are the same as $n_2$ and $z_2$ of formula (1), and $A_3^{n_3-}$ may be the same as $A_2^{n_2-}$ and represents an anion having a valence of $n_3$ other than a phosphate anion, is treated with an aqueous solution of an alkali metal or ammonium salt of a phosphate ion ($H_2PO_4^-$, $HPO_3^{2-}$, or $PO_4^{3-}$) or with an aqueous solution of the $A_2^{n_2-}$ ion shown in formula (1) and the aforesaid phosphate ion to exchange a part or the whole of $A_3^{n_3-}$ with the phosphate ion ($A_2^{n_2-}$ may be the same as $A_3^{n_3-}$).

Examples of the aluminum compound used in the first-mentioned embodiment include aluminum halides such as aluminum chloride, aluminum bromide, aluminum iodide and aluminum fluoride; aluminum sulfate; aluminum nitrate; alkali metal aluminates such as sodium aluminate and potassium aluminate; alcohol salts such as aluminum isopropoxide and aluminum ethylate; and basic aluminum salts such as basic aluminum sulfate, basic aluminum chloride and basic aluminum carbonate.

Examples of the magnesium compounds are magnesium halides such as magnesium fluoride, magnesium chloride, magnesium bromide and magnesium iodide; magnesium sulfate; magnesium nitrate; magnesium perchlorate; magnesium salts of organic acids such as magnesium oxalate, magnesium acetate, magnesium citrate and magnesium tartrate; magnesium oxide; and magnesium carbonate.

Examples of phosphoric acid or its alkali metal or ammonium salts include orthophosphoric acid $H_3PO_4$; monoalkali metal hydrogen phosphates such as monosodium hydrogen phosphate $NaH_2PO_4$ and monopotassium hydrogen phosphate; dialkali metal hydrogen phosphates such as disodium hydrogen phosphate $Na_2HPO_4$, dipotassium hydrogen phosphate $K_2HPO_4$; trialkali metal phosphates such as trisodium phosphate $Na_3PO_4$ and tripotassium phosphate $K_3PO_4$; and mono-, di- and tri-ammonium salts of phosphoric acid such as $NH_4H_2PO_4$, $(NH_4)_2HPO_4$, and $(NH_4)_3PO_4$.

In the first-mentioned embodiment, an alkali is used to adjust the pH of the system to at least 8. Examples of the alkali are alkali metal hydroxides such as sodium hydroxide and potassium hydroxide, alkali metal carbonates such as sodium carbonate and potassium carbonate, calcium hydroxide, ammonia gas, and aqueous ammonia.

If x in formula (1) is smaller than 2, the antacid activity of the resulting hydrotalcite is insufficient, and if it exceeds 40, the pH buffered by the antacid exceeds about 6. Thus, x is suitably $2<x<40$, preferably about $3 \leq x \leq 10$, more preferably $4 \leq x \leq 8$.

In formula (1), each of $A_1^{n_1-}$ and $A_2^{n_2-}$ is not restricted to one kind, but may be a mixture of two or more kinds. As $A_1^{n_1-}$, $HPO_4^{2-}$ is preferred.

In order to have the hydrotalcite of formula (1) exhibit an antacid effect advantageously, $z_2$ is preferably larger than $z_1$. In other words, $A_2^{n_2-}$ is preferably in a major proportion, and $A_1^{n_1-}$, in a minor proportion.

The antacid of this invention may contain various known solid or liquid carriers or diluents and other additives acceptable for use in antacids, and can be formulated into desired dosage forms with or without various adjuvants known in the field of pharmaceuticals.

Examples of dosage forms are dusts, granules, particles, tablets, coated tablets, suspensions, capsules and other orally administrable forms. The pharmaceutical composition in such a dosage form may contain about 5 to about 95% by weight of the compound of formula (1) based on the total weight of the composition.

If required, the antacid of the invention may further contain another antacid, a vitamin preparation, an anti-inflammatory agent, a cardiac, an anti-hypertensive agent, an analgesic, an antihistaminic agent, an antipyretic-analgesic, a digestive, an antitussive, cold pills, a flavor, etc. Or it may be used in combination with these agents or other drugs.

The present invention also provides a method of controlling the pH of gastric juice, which comprises orally administering the phosphate ion-containing hydrotalcite of formula (1) either as such or in the form of a pharmaceutical composition.

The dose of the antacid of the invention can be properly selected depending upon the purpose of administration, the condition of the patient, etc., but may be within the effective range of conventional antacids. For example, the dose is about 10 to about 100 mg/day/kg of body weight as the active component (1) in oral administration.

The antacid of the invention is a useful and uniqued antacid for prevention and treatment of gastritis, chlorhydria, gastric ulcer, and other similar gastric troubles, and exhibits a better action than conventional antacids without involving the side-effects of the conventional antacids.

The following Examples illustrate the present invention more specifically.

EXAMPLE 1

Five liters of a mixed aqueous solution of aluminum chloride and magnesium chloride ($Al^{3+}=0.2$ mole/liter, $Mg^{2+}=0.8$ mole/liter) and 5 liters of an aqueous solution of disodium hydrogen phosphate $Na_2HPO_4$ (0.1 mole/liter) were added at a flow rate of 200 ml/min. by means of a metering pump to a 5-liter cylindrical stainless steel reactor fitted with a stirrer and a pH meter together with a 3 mole/liter aqueous solution of sodium hydroxide. The pH of the reaction mixture was maintained at about 9 to 10, and the reaction was performed continuously. The resulting white precipitate was filtered under reduced pressure, washed fully with water, and dried at about 100° C. for 10 hours. The dried product had the following properties.

X-ray diffraction pattern: identified as hydrotalcite crystals

Chemical composition: $Mg_8Al_2(OH)_{19.5}(HPO_4)_{0.87}\cdot(CO_3)_{0.38}\cdot 5.5H_2O$ Sodium content: 0.006%

The antacid activity of the product was examined by the following testing methods, and the results are shown in Table 1.

[Antacid activity test]

Fuch's test

Fifty milliliters of 0.1-normal hydrochloric acid was put into a 300 ml. beaker, and the beaker was dipped in a constant temperature tank kept at 37±1° C. The electrode of the pH meter was put into it, and the HCl was stirred by a magnetic stirrer. When its temperature reached 37° C., 1.0 g of a sample was put into the beaker. Ten minutes after the addition of the sample, 0.1-N hydrochloric acid was added continuously by means of a metering pump at a rate of 2 ml/min. until the pH of the mixture reached 3 or below. Variations in pH were continuously recorded automatically.

pH stat test

Water (20 ml) was put into a beaker having a volume of about 50 ml. The beaker was put into a constant temperature tank set at 37±1° C. The electrode of the pH meter was put into the beaker, and the water was stirred by a magnetic stirrer. The pH meter was interlockingly connected to a pH stat device. The pH was set at 3.0, and 200 mg of a sample was added. To maintain the pH of this system at 3.0, 1-normal hydrochloric acid was automatically fed to the beaker. The pH and the amount of 1-normal hydrochloric acid fed were automatically recorded as a function of time, and the time which elapsed until 50% and 80% respectively of the sample dissolved in 1-normal hydrochloric acid was measured. The shorter the time measured, the more rapid the reaction of the antacid with the acid.

Rossett-Rice's test 70 ml of 0.1N-HCl and 30 ml of deionized water were put in a 400 ml. beaker. The beaker was then immersed in a constant temperature vessel at 37° C., and the contents were stirred by a magnetic stirrer at a rate of about 200 rpm. To the beaker was added 1.0 g of the sample, and simultaneously, 0.1N-HCl was added at a rate of 4.0 ml per minute. The time and the pH were automatically recorded.

EXAMPLE 2

Five liters of a mixed aqueous solution of magnesium nitrate and aluminum nitrate ($Mg^{2+}=0.6$ mole/liter, $Al^{3+}=0.2$ mole/liter) and a 4 mole/liter aqueous solution of sodium hydroxide were added to a 5-liter cylindrical stainless steel reactor being stirred with a stirrer and containing the electrode of a pH meter dipped therein. The pH of the system was adjusted to 10 to 10.5 by the aqueous solution of sodium hydroxide. The reaction was continuously performed at room temperature. The resulting white precipitate was hydrotalcite having the composition $Mg_6Al_2(OH)_{16}(NO_3)_{1.6}(CO_3)_{0.1}\cdot 2.3H_2O$.

Five hundred grams, calculated as the dry product, of the suspension containing this precipitate was taken, filtered under reduced pressure, and then washed with about 6.5 liters of a 0.2 mole/liter aqueous solution of disodium hydrogen phosphate to ion-exchange $NO_3$ with $HPO_4^{2-}$. The product was washed with water, dehydrated and dried. Chemical analysis of the product showed the following results.

Chemical composition: $Mg_6Al_2(OH)_{15.4}(HPO_4)_{0.84}(CO_3)_{0.46}\cdot 3.74H_2O$ Socium content: 0.002%

X-ray diffraction pattern: identified as hydrotalcite crystals

The antacid activity of this product is shown in Table 1.

EXAMPLE 3

A mixed aqueous solution of magnesium chloride and aluminum chloride ($Mg^{2+}=0.5$ mole/liter, $Al^{3+}=0.2$ mole/liter) and a 4.0 mole/liter aqueous solution of sodium hydroxide were reacted in the same way as in Example 2 to give a hydrotalcite of the formula $Mg_5Al_2(OH)_{14}Cl_2\cdot 3.2H_2O$.

Five hundred grams of the resulting hydrotalcite was washed with 4 liters of a 0.1 mole/liter aqueous solution of trisodium phosphate to ion-exchange Cl by $PO_4^{3-}$. The product was then washed with water and dried to give a product having the following properties.

Chemical composition: $Mg_5Al_2(OH)_{13.67}(PO_4)_{0.71}(CO_3)_{0.10}\cdot 3.1H_2O$ Sodium content: 0.003%

X-ray diffraction pattern: identified as hydrotalcite crystals

The antacid activity of the product is shown in Table 1.

EXAMPLE 4

A hydrotalcite of the following formula $$Mg_4Al_2(OH)_{12}(Cl)_{1.6}(CO_3)_{0.2}\cdot 1.2H_2O$$

was prepared by reacting a mixed aqueous solution of aluminum chloride and magnesium chloride ($Al^{3+}=0.3$ mole/liter, $Mg^{2+}=0.6$ mole/liter) and a 3 mole/liter aqueous solution of sodium hydroxide in the same way as in Example 2.

Five hundred grams of this hydrotalcite was washed with 4 liters of 0.4 mole/liter monosodium hydrogen phosphate and subsequently with 4 liters of 0.2 mole/liter of sodium carbonate to perform ion exchange. The product was washed with water and dried. The product had the following properties.

Chemical composition: $Mg_4Al_2(OH)_{12}(H_2PO_4)_{0.7}(CO_3)_{0.6}\cdot 0.08H_2O$ Sodium content: 0.008%

X-ray diffraction pattern: identified as hydrotalcite

The antacid activity of the product is shown in Table 1.

EXAMPLE 5

A mixed aqueous solution of aluminum chloride and magnesium chloride ($Al^{3+}=0.2$ mole/liter, $Mg^{2+}=0.6$ mole/liter) and 3N sodium hydroxide were fed into a 2-liter stainless steel reactor at a rate of about 80 ml/min. and 46 ml/min., respectively, by means of metering pumps. With thorough stirring, the reaction was carried out while maintaining the pH at about 10.0 to 10.4. The reactor was immersed in a constant temperature vessel at 40±1° C., and the reaction temperature was controlled to this temperature range. The resulting precipitate was filtered, washed with water, and then dried at 100° C. for 10 hours. By a powder X-ray diffraction method, this product was found to show much the same X-ray diffraction pattern as hydrotalcite. Its chemical analysis showed the following composition.

$$Mg_6Al_2(OH)_{16}Cl_{1.8}(CO_3)_{0.1}\cdot 4.1H_2O$$

One hundred grams of the resulting Cl-type hydrotalcite powder was suspended in 500 ml of water and filtered. Subsequently, the product was washed with 0.1 mole/liter aqueous $Na_2HPO_4$ solution (about 30° C.) in an amount such that the equivalent ratio of $HPO_4^{2-}$ to Cl became 0.15, thereby performing ion-exchange reaction. The product was further washed with 0.2 mole/liter aqueous $Na_2CO_3$ solution in an amount such that the equivalent ratio of $CO_3^{2-}$ to Cl became 0.9, followed by washing with water. The washed product was dried at 100° C. for 15 hours. Its chemical analysis showed the following chemical composition.

$$Mg_{6.1}Al_2(OH)_{15.76}(HPO_4)_{0.10}(CO_3)_{1.12}\cdot 3.7H_2O$$

By a powder X-ray diffraction method, the resulting product was found to have much the same X-ray diffraction pattern as hydrotalcite. The activity of the product as an antacid was evaluated in the same way as in Example 1. The results are shown in Table 2.

EXAMPLES 6 TO 9

In each run, the same Cl-type hydrotalcite as obtained in Example 5 was washed successively with 0.1 mole/liter aqueous $Na_2HPO_4$ solution and 0.2 mole/liter $Na_2CO_3$ solution at the equivalent ratios tabulated below, and dried. The product was then washed with water and dried. The products were tested for antacid activity in the same way as in Example 1, and the results are shown in Table 2.

TABLE 1

| | Fuch's test | | | | pH stat test | | Rossett-Rice's test | |
| | | | | | $T_{50}$[5] | $T_{80}$[6] | | |
| Example | Time required[1] until the pH reached 3 (seconds) | Time required[2] until the pH reached 3.5 (seconds) | Maximum[3] pH | Duration time[4] the pH was buffered to more than 3 (minutes) | (the time required until 50% was reacted) (seconds) | (the time required until 80% was reacted) (seconds) | Time required[7] until the pH reached 3 (seconds) | Duration time[8] the pH was buffered to 3–5 (minutes) |
|---|---|---|---|---|---|---|---|---|
| 1 | 3 | 5 | 5.5 | 84 | 30 | 80 | 10 | 43.6 |
| 2 | 5 | 7 | 4.8 | 79 | 100 | 260 | 12 | 42.5 |
| 3 | 8 | 10 | 4.1 | 77 | 230 | 435 | 15 | 41.2 |
| 4 | 12 | 19 | 4.2 | 86 | 90 | 176 | 18 | 44.1 |

Note
In (1), (2), (5), (6) and (7), larger values show better properties as an antacid.
In (3), pH values in the range of 3 to 5 show a better antacid.
In (4) and (8), larger values show better properties as an antacid.
The above note applies also to Table 2 given hereinbelow.

The products were found to have the following composition formulae.

Example 6: $Mg_{6.3}Al_2(OH)_{16.32}(HPO_4)_{0.16}(CO_3)_{0.98}\cdot 3.6H_2O$

Example 7: $Mg_6Al_2(OH)_{15.92}(HPO_4)_{0.24}(CO_3)_{0.80}\cdot 3.9H_2O$

Example 8: $Mg_6Al_2(OH)_{15.74}(HPO_4)_{0.36}(CO_3)_{0.77}\cdot 4.2H_2O$

Example 9: $Mg_{5.8}Al_2(OH)_{13.46}(HPO_4)_{0.42}(CO_3)_{0.85}\cdot 3.2H_2O$

| Example | Equivalent of 0.1 mole/liter aqueous $Na_2HPO_4$ solution to Cl | Equivalent of 0.2 mole/liter aqueous $Na_2CO_3$ solution to Cl |
|---|---|---|
| 6 | 0.20 | 0.85 |
| 7 | 0.30 | 0.80 |

| Example | Equivalent of 0.1 mole/liter aqueous Na$_2$HPO$_4$ solution to Cl | Equivalent of 0.2 mole/liter aqueous Na$_2$CO$_3$ solution to Cl |
|---|---|---|
| 8 | 0.40 | 0.75 |
| 9 | 0.50 | 0.70 |

EXAMPLE 10

A 1.0 mole/liter aqueous solution of sodium aluminate, a 1.5 mole/liter aqueous solution of magnesium nitrate and a 2N aqueous solution of sodium hydroxide were reacted at a pH of 9.6 to 9.8 and a temperature of 30±1° C. by the same procedure as in Example 1. By chemical analysis the resulting precipitate was found to have the following composition.

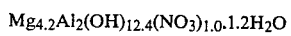
$Mg_{4.2}Al_2(OH)_{12.4}(NO_3)_{1.0}\cdot1.2H_2O$

Two liters of the product slurry obtained as above was dehydrated under reduced pressure, and subsequently, washed with a 0.2 mole/liter aqueous solution of K$_2$HPO$_4$ and a 0.1 mole/liter aqueous solution of K$_2$CO$_3$ in this order in an amount such that the equivalent ratios of these compound were 0.2 and 0.9, respectively, to NO$_3$. The product was washed with water and then dried at 100° C. for 10 hours. By powder X-ray diffraction analysis, the dried product was found to have much the same X-ray diffraction pattern as hydrotalcite. Chemical analysis showed it to have the following composition.

$Mg_{4.2}Al_2(OH)_{12.36}(HPO_4)_{0.15}(CO_3)_{0.87}\cdot2.8H_2O$

The activity of this product as an antacid was evaluated in the same way as in Example 1, and the results are shown in Table 2.

EXAMPLE 11

A 4-liter reactor was charged with 1 liter of a mixed aqueous solution of magnesium chloride and aluminum sulfate (Mg$^{2+}$=0.8 mole/liter, Al$^{3+}$=0.2 mole/liter) and 300 ml of a 0.2 mole/liter aqueous solution of (NH$_4$)$_2$HPO$_4$ together with a 2 mole-liter aqueous solution of sodium hydroxide, and with thorough stirring, the reaction was carried out at a pH of about 10.2 and a temperature of about 20±2° C. The resulting product slurry was dehydrated under reduced pressure, washed with 400 ml of a 0.2 mole/liter aqueous solution of Na$_2$CO$_3$, and washed with water, and dried. By a powder X-ray diffraction analysis, the dried product was found to have much the same X-ray diffraction pattern as hydrotalcite. By chemical analysis, this product was found to have the following composition.

$Mg_8Al_2(OH)_{19.78}(HPO_4)_{0.28}(CO_3)_{0.83}\cdot4.8H_2O$

The product was tested in the same way as in Example 1, and the results are shown in Table 2.

EXAMPLE 12

With thorough stirring, 1 liter of a 1.0 mole/liter aqueous solution of potassium aluminate, 2 liters of a 1.25 mole/liter aqueous solution of magnesium chloride and a 2 mole/liter aqueous solution of potassium hydroxide were simultaneously added to a 5-liter reactor, and the pH of the mixture was maintained at about 9.8 to 10.0 by the addition of the potassium hydroxide solution. The resulting precipitate was dehydrated under reduced pressure, and then washed with 300 ml of a 0.2 mole/liter aqueous solution of Na$_2$HPO$_4$ and 450 ml of a 0.2 mole/liter aqueous solution of Na$_2$CO$_3$ and then with water, and dried.

The product was found to have much the same powder X-ray diffraction pattern as hydrotalcite. It had the following chemical composition.

$Mg_5Al_2(OH)_{13.94}(HPO_4)_{0.12}(CO_3)_{0.91}\cdot3.6H_2O$

The product was tested in the same way as in Example 1, and the results are shown in Table 2.

COMPARATIVE EXAMPLE 1

Example 1 of U.S. Pat. No. 2,958,626 was followed, and the product was tested in the same way as in Example 1 of this application. The results are shown in Table 2.

COMPARATIVE EXAMPLE 2

Example 1 of U.S. Pat. No. 3,099,524 was followed, and the product was tested in the same way as Example 1 of the present application. The results are shown in Table 2.

COMPARATIVE EXAMPLE 3

Example 18 of U.S. Pat. No. 3,879,525 was followed, and the product was tested in the same way as in Example 1 of the present application. The results are shown in Table 2. The product had the chemical composition Mg$_6$Al$_2$(OH)$_{16}$HPO$_4\cdot$4H$_2$O.

EXAMPLE 13

The same Cl-type hydrotalcite as obtained in Example 5 was washed with a 0.1 mole/liter aqueous solution of Na$_2$HPO$_4$ and a 0.2 mole/liter aqueous solution of sodium tartrate in this sequence in amounts corresponding to 0.2 and 1.0 equivalent respectively to 1 equivalent of Cl. The product was then washed with water and dried in the same way as in Example 5. The product was tested in the same way as in Example 1, and the results are shown in Table 2.

The resulting product was found to have the following chemical composition.

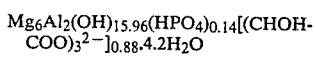
$Mg_6Al_2(OH)_{15.96}(HPO_4)_{0.14}[(CHOHCOO)_3{}^{2-}]_{0.88}\cdot4.2H_2O$

TABLE 2

| Example | Fuch's test Time required[1] until the pH reached 3 (seconds) | Fuch's test Time required[2] until the pH reached 3.5 (seconds) | Maximum[3] pH | Duration time[4] the pH was buffered to more than 3 (minutes) | pH stat test T50[5] (the time required until 50% was reacted) (seconds) | pH stat test T80[6] (the time required until 80% was reacted) (seconds) | Rossett-Rice's test Time required[7] until the pH reached 3 (seconds) | Rossett-Rice's test Duration time[8] the pH was buffered to 3–5 (minutes) |
|---|---|---|---|---|---|---|---|---|
| 5 | 3 | 4 | 4.6 | 120 | 41 | 87 | 7 | 54.1 |
| 6 | 3 | 4 | 4.5 | 118 | 45 | 90 | 7 | 54.0 |
| 7 | 4 | 6 | 4.6 | 106 | 52 | 105 | 8 | 47.2 |
| 8 | 4 | 6 | 4.4 | 98 | 62 | 123 | 8 | 46.6 |
| 9 | 4 | 6 | 4.5 | 90 | 71 | 213 | 8 | 44.6 |
| 10 | 8 | 10 | 4.1 | 100 | 104 | 265 | 13 | 46.7 |
| 11 | 3 | 5 | 5.3 | 109 | 29 | 62 | 6 | 52.4 |
| 12 | 7 | 9 | 4.2 | 132 | 95 | 234 | 11 | 57.4 |
| 13 | 3 | 5 | 4.5 | 121 | 47 | 88 | 7 | 54.4 |
| Comp. Ex. 1 | 78 | 91 | 3.6 | 68 | 255 | 695 | 82 | 38.4 |
| Comp. Ex. 2 | 73 | 87 | 3.4 | 62 | 294 | 941 | 76 | 34.3 |
| Comp. Ex. 3 | 10 | 21 | 3.9 | 57 | 248 | 632 | 12 | 26.4 |

What we claim is:

1. A pharmaceutical composition comprising an amount, effective as an antacid, of a phosphate ion-containing hydrotalcite of the following formula $$Mg_xAl_2(OH)_{2x+6-n_1z_1-n_2z_2}(A_1^{n_1-})_{z_1}(A_2^{n_2-})_{z_2} \cdot mH_2O$$

wherein $A_1^{n_1-}$ represents at least one anion having a valence of $n_1$ selected from the group consisting of $H_2PO_4^-$ and $HPO_4^{2-}$, and $PO_4^{-3}$, $A_2^{n_2-}$ represents at least one anion having a valence of $n_2$ other than the $A_1^{n_1-}$, selected from the group consisting of $CO_3^{2-}$, tartrate ion $(CHOHCOO)_2^{2-}$, salicylate ion $C_6H_5(OH)COO^-$, citrate ion $C_3H_4OH(COO)_3^{3-}$, glycine ion $NH_2CH_2COO^-$, glutamate ion $C_5H_7NO_4^{2-}$, cystine ion $C_3H_6NO_2S^-$, lactate ion $CH_3CHOHCOO^-$ and malate ion $CHOHCH_2(COO)_2^{2-}$, and x, $z_1$, $z_2$, and m are positive numbers satisfying the following expressions $2 < x < 40$, $0.05 \leq z_1 \leq 2$, $0.1 \leq z_2 \leq 2$ $0 < m < 40$, $0.5 \leq z_1 + z_2 \leq 2$, and a pharmaceutically acceptable diluent or carrier.

2. The composition of claim 1 which is in an orally administrable dosage form.

3. A method for controlling the pH of gastric juice, which comprises orally administering a phosphate ion-containing hydrotalcite of the formula $$Mg_xAl_2(OH)_{2x+6-n_1z_1-n_2z_2}(A_1^{n_1-})_{z_1}(A_2^{n_2-})_{z_2} \cdot mH_2O$$

wherein $A_1^{n_1-}$ represents at least one anion having a valence of $n_1$ selected from the group consisting of $H_2PO_4^-$, $HPO_4^{2-}$ and $PO_4^{-3}$, $A_2^{n_2-}$ represents at least one anion having a valence of $n_2$ other than the $A_1^{n_1-}$, selected from the group consisting of $CO_3^{2-}$, tartrate ion $(CHOHCOO)_2^{2-}$, salicylate ion $C_6H_5(OH)COO^-$, citrate ion $C_3H_4OH(COO)_3^{3-}$, glycine ion $NH_2CH_2COO^-$, glutamate ion $C_5H_7NO_4^{2-}$, cystine ion $C_3H_6NO_2S^-$, lactate ion $CH_3CHOHCOO^-$ and malate ion $CHOHCH_2(COO)_2^{2-}$, and x, $z_1$, $z_2$, and m are positive numbers satisfying the following expressions $2 < x < 40$ $0.05 \leq z_1 \leq 2$, $0.1 \leq z_2 < 2$, $0 < m < 40$, $0.5 \leq z_1 + z_2 \leq 2$.

4. A compound of the following formula which is useful in controlling the pH of gastric juice $$Mg_xAl_2(OH)_{2x+6-n_1z_1-n_2z_2}(A_1^{n_1-})_{z_1}(A_2^{n_2-})_{z_2} \cdot mH_2O$$

wherein $A_1^{n_1-}$ represents at least one anion having a valence of $n_1$ selected from the group consisting of $H_2PO_4^-$, $HPO_4^{2-}$ and $PO_4^{-3}$, $A_2^{n_2-}$ represents at least one anion having a valence of $n_2$ other than the $A_1^{n_1-}$, selected from the group consisting of $CO_3^{2-}$, tartrate ion $(CHOHCOO)_2^{2-}$, salicylate ion $C_6H_5(OH)COO^-$, citrate ion $C_3H_4OH(COO)_3^{3-}$, glycine ion $NH_2CH_2COO^-$, glutamate ion $C_5H_7NO_4^{2-}$, cystine ion $C_3H_6NO_2S^-$, lactate ion $CH_3CHOHCOO^-$ and malate ion $CHOHCH_2(COO)_2^{2-}$, and x, $z_1$ and $z_2$, and m are positive numbers satisfying the following expressions $2 < x < 40$, $0.05 \leq z_1 \leq 2$, $0.1 \leq z_2 < 2$, $0 < m < 40$, $0.5 \leq z_1 + z_2 \leq 2$.

5. The method of claim 3 wherein the phosphate ion-containing hydrotalcite is administered at a dose of from about 10 to about 100 mg/day/kg of body weight.

6. The composition of claim 1 wherein the phosphate ion-containing hydrotalcite is present in an amount of from about 5 to about 95% by weight based on the total weight of the composition.

7. The composition of claim 1 wherein $z_2$ is larger than $z_1$.

8. The composition of claim 1 wherein x, $z_1$ and $z_2$ are positive numbers satisfying the following expressions $$3 \leq x \leq 10$$

$$0.08 \leq z_1 \leq 1,$$

$$0.1 \leq z_2 < 1.5,$$

$$0.5 \leq m < 40,$$

$$0.8 \leq z_1 + z_2 \leq 1.5.$$

9. The composition of claim 8 wherein $$4 \leq x \leq 8,$$

$$0.1 \leq z_1 \leq 0.5$$

$$0.5 \leq z_2 \leq 1.2.$$

* * * * *